United States Patent
Jheengut et al.

(10) Patent No.: US 9,725,392 B2
(45) Date of Patent: Aug. 8, 2017

(54) EFFICIENT SCALABLE SYNTHESES OF ABSCISIC ACID, 8'-ACETYLENE ABSCISIC ACID AND 8'-CYCLOPROPYL ABSCISIC ACID

(71) Applicant: NATIONAL RESEARCH COUNCIL OF CANADA, Ottawa (CA)

(72) Inventors: Vishal Jheengut, Saskatoon (CA); Ken M. Nelson, Warman (CA); Suzanne R. Abrams, Saskatoon (CA)

(73) Assignee: NATIONAL RESEARCH COUNCIL OF CANADA, Ottawa, Ontario (CA)

( * ) Notice: Subject to any disclaimer, the term of this patent is extended or adjusted under 35 U.S.C. 154(b) by 0 days.

(21) Appl. No.: 15/241,564

(22) Filed: Aug. 19, 2016

(65) Prior Publication Data
US 2017/0057899 A1 Mar. 2, 2017

Related U.S. Application Data

(60) Provisional application No. 62/210,477, filed on Aug. 27, 2015.

(51) Int. Cl.
*C07C 51/09* (2006.01)
*C07C 46/06* (2006.01)
(Continued)

(52) U.S. Cl.
CPC ............ *C07C 51/09* (2013.01); *C07C 46/06* (2013.01); *C07C 67/40* (2013.01); *C07C 67/327* (2013.01);
(Continued)

(58) Field of Classification Search
None
See application file for complete search history.

(56) References Cited

U.S. PATENT DOCUMENTS 5,201,931 A * 4/1993 Abrams ................ A01N 37/36
504/193
5,518,995 A * 5/1996 Abrams ................ A01N 35/06
504/193
(Continued)

FOREIGN PATENT DOCUMENTS

WO 2005108345 A1 11/2005

OTHER PUBLICATIONS

Balko, T. W., et al., Total synthesis of -8'-trifluoromethyl abscisic acid, 1999, Tetrahedron Letters, vol. 40, pp. 6347-6351.*
(Continued)

*Primary Examiner* — Yate K Cutliff
(74) *Attorney, Agent, or Firm* — Bereskin & Parr LLP/S.E.N.C.R.L., s.r.l.; Patricia Folkins

(57) ABSTRACT

Methods are provided for synthesis of abscisic acid and 8' analogues thereof (including an enantiopure 8'-acetylene analogue) including methods wherein the previously reported first step of oxidation of 2,6-dimethylphenol (VI) to 2,6-dimethylbenzoquinone, mono ketal (VII) is replaced by a novel two step process comprising (i) oxidation of 2,6-dimethylphenol (VI) using potassium peroxymonosulfate with a catalytic amount of iodobenzene to produce 2,6-dimethylbenzoquinone (XVI) and (ii) ketalization of 2,6-dimethylbenzoquinone (XVI) using ethylene glycol, trimethylorthoformate with a catalytic amount of p-toluenesulfonic acid to produce 2,6-dimethylbenzoquinone, mono ketal (VII).

12 Claims, 3 Drawing Sheets

(51) Int. Cl.
  *C07C 67/40* (2006.01)
  *C07C 67/327* (2006.01)
  *C07C 403/16* (2006.01)
(52) U.S. Cl.
  CPC ........ *C07C 403/16* (2013.01); *C07C 2101/16* (2013.01)

(56) References Cited

U.S. PATENT DOCUMENTS 6,004,905 A * 12/1999 Abrams ................ A01N 49/00
  504/193
2008/0200339 A1   8/2008 Abrams et al.

OTHER PUBLICATIONS

Lei, B., et al., Achiral cyclohexadienone analogues of abscisic acid: Synthesis and biological activity, 1994, Phytochemistry, vol. 37, No. 2, pp. 289-296.*
Alexakis, A., et al. "Dramatic Improvement of the Enantiomeric Excess in the Asymmetric Conjugate Addition Reaction Using new Experimental Conditions", J. Am. Chem. Soc., 2002, 124, pp. 5262-5263.
Abrams, Suzanne R., et al., "Deuterated abscisic acid analogs for mass spectrometry and metabolism studies", Journal of Labelled Compounds and Radiopharmaceuticals, 2003, 46, pp. 273-283.
Abrams, Suzanne R., et al., "8'-Methylene Abscisic Acid—An Effective and Persistent Analog of Abscisic Acid", Plant Physiol, 1997, 114, pp. 89-97.
Corey, E.J., et al., "New Methods for the Oxidation of Aldehydes to Carboxylic Acids and Esters", J. Am. Chem. Soc., 90:20, Sep. 25, 1968, pp. 5616-5617.
Cui, Sheng, et al., "Practical Asymmetric Conjugate Alkynylation of Meldrum's Acid-Derived Acceptors: Access to Chiral β-Alkynyl Acids", J. Am. Chem. Soc., 2010, 132, pp. 436-437.
Cutler, Adrian J. et al, "Inhibitors of Abscisic Acid 8'-Hydroxylase", Biochemistry, 2000, 39, pp. 13614-13624.
Delapierre, Guillaume, et al., "Enantioselective Conjugate Addition of Diethylzinc to Enones with Chiral Copper-QUIPHOS Catalyst—Influence of the Addition of Water on the Enantioselectivity", Eur. J. Org. Chem., 2000, pp. 2507-2511.
Franck-Neumann, M. et al, Synthese Cyclopropenique De Derives De L'Illudine M., Tetrahedron Letters, 1989, vol. 30, No. 27, pp. 3537-3540, English Abstract.
Harutyunyan, Syuzanna R., et al, "Catalytic Asymmetric Conjugate Addition and Allylic Alkylation with Grignard Reagents", Chem. Rev. 2008, 108, pp. 2824-2852.
Hawner, Christine, et al., "Metal-catalyzed asymmetric conjugate addition reaction: formation of quaternary stereocenters", Chem. Commun., 2010, 46, pp. 7295-7306.
Imbos, Rosalinde, et al., "A catalytic enantioselective route to cis- and trans-3,4,4,5-tetrasubstituted cyclohexanones; remarkable chiral catalyst control in sequential cataltic 1,4-additions to cyclohexadienones", Tetrahedron, 57, 2001, pp. 2485-2489.

Breit, Bernhard et al., "Copper-mediated Diastereoselective Conjugate Additions and Allylic Substitution Reactions", in Modern Organocopper Chemistry, Krause, Norbert (Ed), Wiley-VCH Verlag GmbH; Weinghem, Germany, 2002, Chapter 6, pp. 188-223.
Lei, Bo et al, "Achiral Cyclohexadienone Analogues of Abscisic Acid: Synthesis and Biological Activity", Phytochem., vol. 37, No. 2, 1994, pp. 289-296.
Merino Estibaliz, et al., "Stereocontrolled Approach to Phenyl Cyclitols from (SR-[(p-Tolylsulfinyl)methyl]-p-quinol", J. Org. Chem., 2009, 74, pp. 2824-2831.
Minisci, Francesco, et al., "Facile and Convenient Syntheses of Quinones from Phenols", J. Org. Chem., 1989, 54 (3), pp. 728-731.
Nyangulu, James M. et al, "Synthesis and biological activity of tetralone abscisic acid analogues", Org. Biomol. Chem., 2006, 4, pp. 1400-1412.
Ohkuma, K. "The Structure of Abscisin II", Tetrahedron Letters, 1965, 6 (29), pp. 2529-2535.
Rose, Patricia A., et al,. "8'-Acetylene ABA: An Irreversible Inhibitor of ABA 8'-Hydroxylase", Biorganic & Medicinal Chemistry Letters, 1997, vol. 7, No. 19. pp. 2543-2546.
Sakaino, Makoto et al, "Diels-Alder Reactions of Vinylbicyclo[4.1.0] Heptenes", Tetrahedron Letters, vol. 28, No. 28, 1987, pp. 3201-3204.
Tohma Hirofumi, et al, "Novel and efficient synthesis of p-quinones in water via oxidative demethylation of phenol ethers using hypervalent iodine(III) reagents" Tetrahadron Letters, 42 (39), 2001, pp. 6899-6902.
Yakura, Takayuki et al., "Efficient Synthesis of p-Quinols Using Catalytic Hypervalent Iodine Oxidation of 4-Arylphenols with 4-lodophenoxyacetic Acid and Oxone", Chem. Pharm. Bull., 57(6), 2009, pp. 643-645.
Zagulyaeva, Aleksandra A., et al., "Hofmann Rearrangement of Carboxamides Medicated by Hypervalent Iodine Species Generated in Situ from Iodobenzene and Oxone: Reaction Scope and Limitations", Organic Letters, 2010, vol. 12, No. 20, pp. 4644-4647.
Rose, Patricia A. et al, "Chiral Synthesis of (+)-8'-demethyl abscisic acid", Canadian Journal of Chemistry, 1996, 74(10), pp. 1836-1843.
Solomon, Mark et al, "Ligand Assisted Nucleophilic Additions. Control of Site and Face Attack of Nucleophiles on 4-Oxidoenones", J. Am. Chem. Soc., 1988, 110, pp. 3702-3704.
Walker-Simmons M., "Enhancement of ABA responsiveness in wheat embryos by high temperature" Plant, Cell and Environment, 1988, 11, pp. 769-775.
Fujimori, Shinji, et al., "Stereoselective Conjugate Addition Reactions Using in Situ Metallated Terminal Alkynes and the Development of Novel Chiral P,N-Ligands", Bull. Chem. Soc. Jpn. vol. 80, No. 9, 2007, pp. 1635-1657.
Feringa, Ben L., et al., "Copper-catalyzed Enantioselective Conjugagte Addition Reactions of Organozinc Reagents", in Modern Organocopper Chemistry, Krause, Norbert (Ed), Wiley-VCH Verlag GmbH; Weinghem, Germany, 2002, Chapter 7, pp. 224-259.
Yakura, Takayuki, et al., "Catalytic Hypervalent Iodine Oxidation Using 4-Iodophenoxyacetic Acid and Oxone: Oxidation of p-Alkoxyphenols to p-Benzoquinones", Chem. Pharm. Bull. 57(3), 2009, pp. 252-256.

* cited by examiner

EFFICIENT SCALABLE SYNTHESES OF ABSCISIC ACID, 8'-ACETYLENE ABSCISIC ACID AND 8'-CYCLOPROPYL ABSCISIC ACID

CROSS REFERENCE TO RELATED APPLICATION

This application claims the benefit of U.S. Provisional Application No. 62/210,477 filed Aug. 27, 2015.

FIELD OF THE INVENTION

The invention relates, in general, to the field of plant hormones and, in particular, to a method of synthesizing abscisic acid, 8'-acetylene abscisic acid and 8'-cyclopropyl abscisic acid.

BACKGROUND OF THE INVENTION

Abscisic acid (ABA, I) is a plant hormone that regulates diverse aspects of growth and development. In higher plants including seed germination and maturation, regulation of stomatal opening, root and shoot growth and transpiration. It also plays a role in plant tolerance and adaptation to environmental stresses such as drought, cold or excess salinity.

The two-dimensional structure of ABA (I) was first elucidated In the 1960's to be a monocyclic sesquiterpene and verified by its racemic synthesis (Ohkuma, K.; Addicott, F. T.; Smith, O. E.; Thiessen, W. E., *Tetrahedron Letters* 1965, 6 (29), 2529-2535). The absolute stereochemistry of ABA (I) was later determined to be S-ABA (I), as shown below (Ryback, G., *Journal of the Chemical Society, Chemical Communications* 1972, (21), 1190-1).

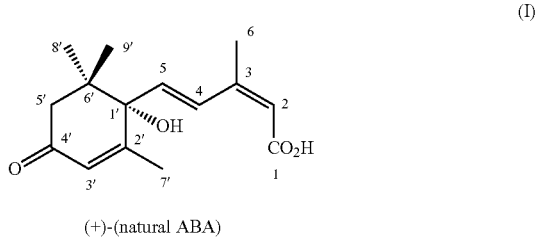

(+)-(natural ABA)

Plant receptors for ABA (I) have been elusive and have been identified only recently. ABA (I) may be applied externally to plants to provide certain desired effects such as maintaining dormancy of buds, improving thinning, accelerating defoliation or enhancing colour development of fruits. However, ABA (I) has found limited use as an externally applied plant growth regulator because it is easily catabollzed so that its effects are short-lived.

The principal catabolic pathway of ABA (I) in plants involves hydroxylation at the 8'-methyl carbon (following the conventional ABA numbering system) mediated by the enzyme P450 monooxygenase (+)-S-ABA 8'-hydroxylase. An intermediate, 8'-hydroxy ABA (II), is formed which undergoes reversible intramolecular Michael addition to form biologically inactive (−)-phaseic acid (III).

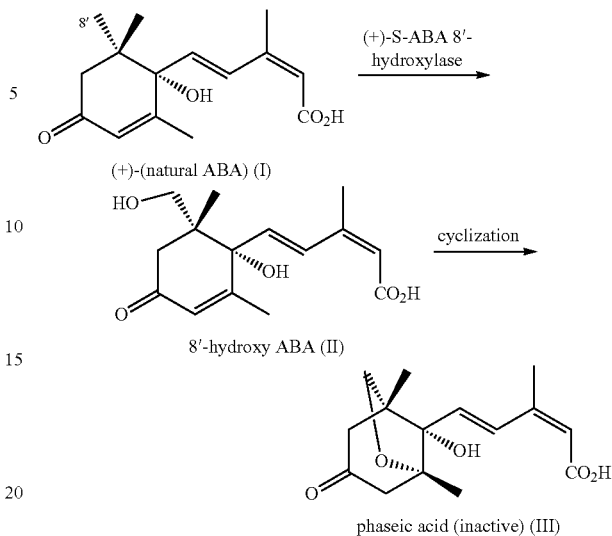

In recent years, synthetic analogues of ABA (I) have been developed with a view to designing compounds having greater potency and less susceptibility to catabolic degradation. Some features of the ABA molecule appear to be required for activity, particularly, the carboxyl and ketone groups, the six-membered ring, the 7'-methyl group and the 2-Z double bond of the side chain. Other parts of the molecule can be modified without a loss of activity. For example, the ring double bond, both the 8'- and 9'-methyl groups and the 4-E double bond of the side chain each can be altered and the resultant analogue retains activity.

Many synthetic analogues of ABA have been reported. For example, U.S. Pat. No. 6,004,905 discloses a family of 8'- and 9'-ABA analogues having a hydrocarbon group at the 8'- or 9'-position. Also disclosed is a method of synthesizing these analogues. US 2008/0200339 discloses bicyclic ABA analogues and a process for their production. Some of the varied analogues disclosed include hydroxylation at the C-8' or C-9' positions and a wide variety of substitutions at the C-8' position.

Recently, it has been shown that replacing the 8'-methyl group of ABA with an acetylene group resulted in an analogue (compound (+)-(IV)) having 10 to 30 times greater anti-transperant and growth inhibition activities than natural ABA due to greater persistence in plants and weak irreversible inhibition of the enzyme (+)-S-ABA 8'-hydroxylase (Cutler, A. J, of al. (2000) Biochemistry. 39, 13614-13624.).

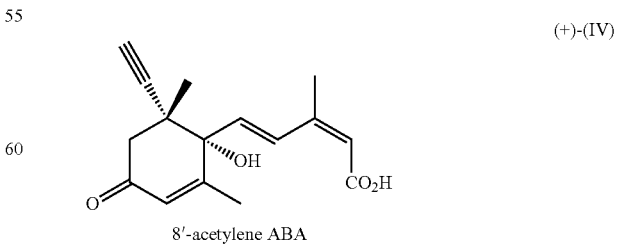

8'-acetylene ABA

Similarly, an 8'-cyclopropyl analogue (+)-(V) shows high biological activity.

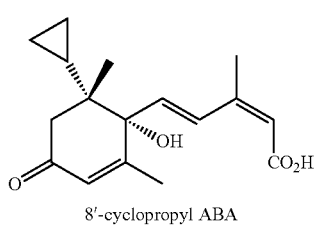

8'-cyclopropyl ABA (+)-(V)

Previously reported processes for synthesis of ABA and its analogues required eight distinct steps and eight separate work-up procedures. (Lei, of al. (1994) *Phytochem.* 37, 289-296.; Rose et al. (1997) *Bioorg. Med. Chem. Lett.* 7, 2543-2546.) As a result, the processes are costly and inefficient, and are not well adapted for use on an industrial scale. The previously reported process is as follows:

1.

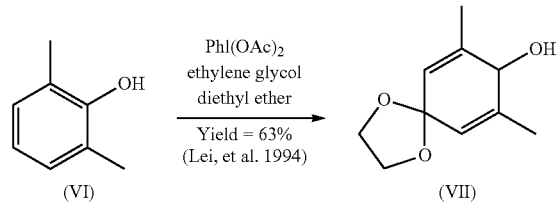

(VI) → (VII)

PhI(OAc)$_2$
ethylene glycol
diethyl ether

Yield = 63%
(Lei, et al. 1994)

2.

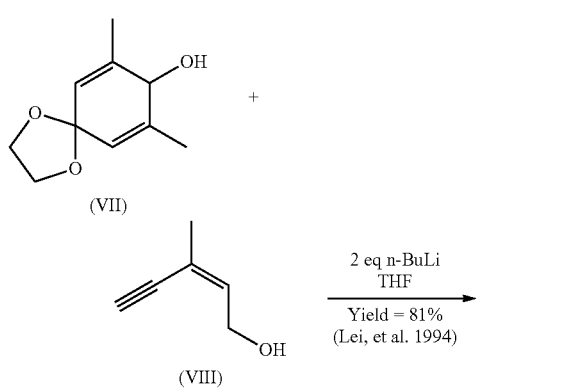

(VII) + (VIII)

2 eq n-BuLi
THF

Yield = 81%
(Lei, et al. 1994)

→ (IX)

3.

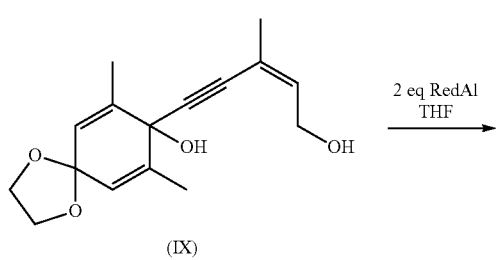

(IX)

2 eq RedAl
THF

→

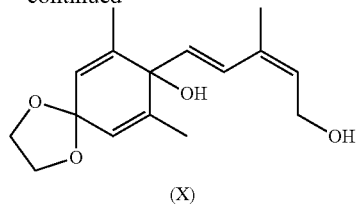

(X)

4.

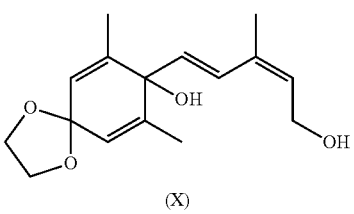

(X)

20 eq MnO$_2$
acetone

→

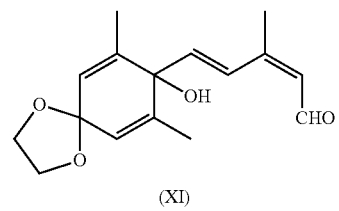

(XI)

5.

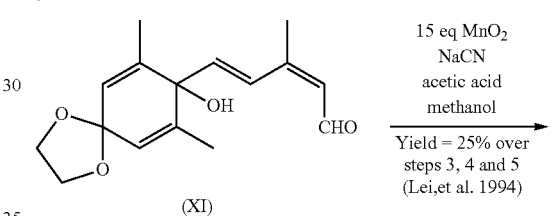

(XI)

15 eq MnO$_2$
NaCN
acetic acid
methanol

Yield = 25% over
steps 3, 4 and 5
(Lei, et al. 1994)

→

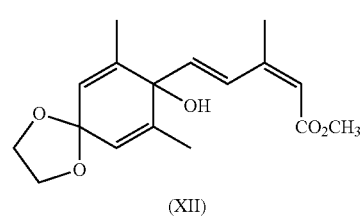

(XII)

6.

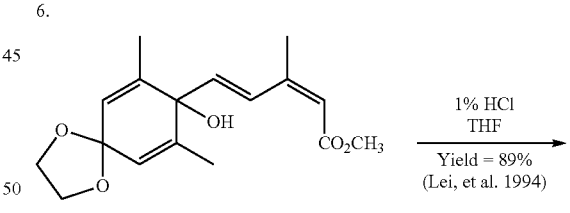

(XII)

1% HCl
THF

Yield = 89%
(Lei, et al. 1994)

→

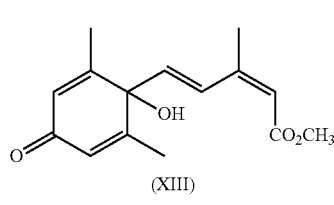

(XIII)

7.

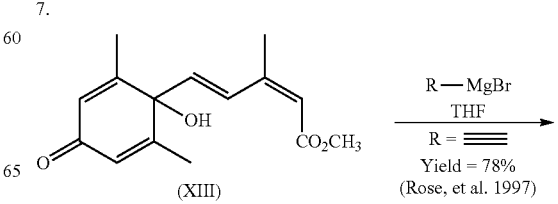

(XIII)

R—MgBr
THF
R = ≡≡≡

Yield = 78%
(Rose, et al. 1997)

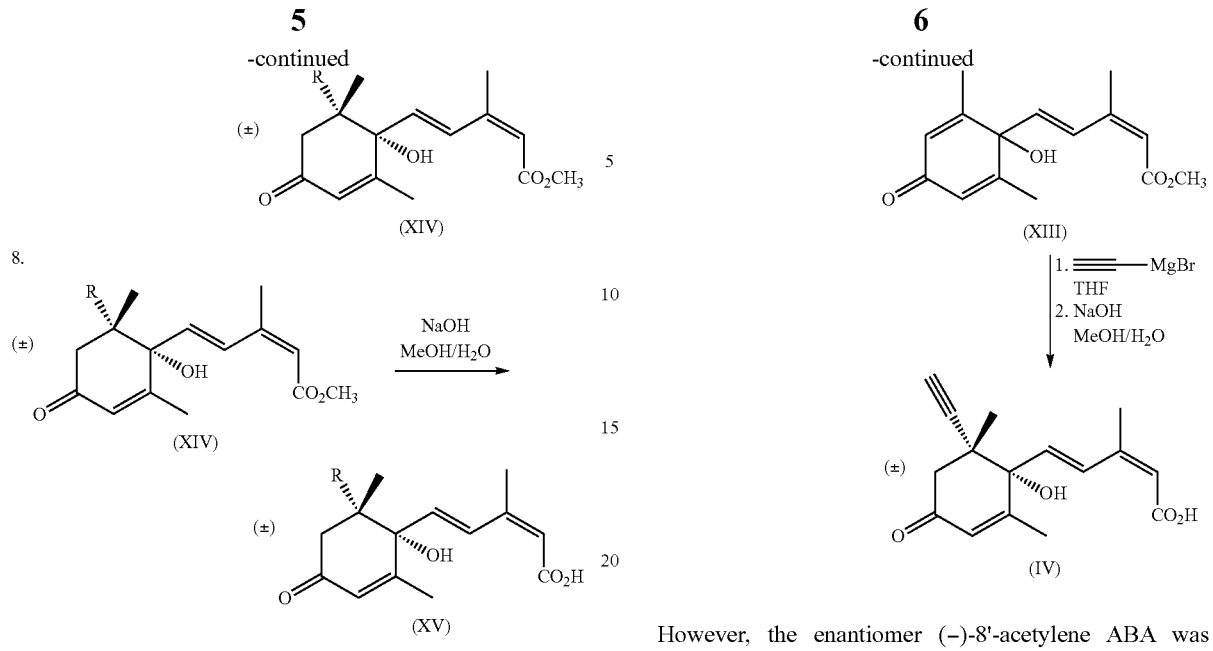

The first step in the previously reported synthetic process, production of 2,6-dimethyl-1,4-benzoquinone, mono ketal (VII), consisted of oxidation of 2,6-dimethylphenol (VI) using iodobenzene diacetate in ethylene glycol to give a monoketal protected benzoquinone (Lei, et al. (1994) Phytochem. 37, 289-296. ). This step has many drawbacks that render it unsuitable for use in an industrial process. It is difficult to scale-up on the bench top beyond 100 g. Furthermore, iodobenzene diacetate is too expensive to use for the synthesis of an agrochemical, which must be produced on an industrial scale. A byproduct of the reaction is a stoichiometric amount of iodobenzene that must be removed by distillation under reduced pressure. Also, the reaction generates a number of side products of the phenol that required column chromatography to remove. Accordingly, a need exists for a synthetic process having a more efficient and economical oxidation step.

The previously reported process also utilizes many discrete steps, which require the use of different reactants and different reaction vessels. Accordingly, a need exists for a simplified process which is suitably efficient to be used on an industrial scale.

Further, previously reported processes for synthesis of ABA and ABA analogues resulted in the manufacture of a racemic mixture (i.e. a 1:1 mixture containing both enantiomers of a chiral compound). A process for synthesis of racemic (±)-8'-acetylene ABA (±)-(IV) starting from two simple starting units (VII) and (VIII) has been previously reported, and is shown below (Rose et al. (1997) Bioorg. Med. Chem. Lett. 7, 2543-2546. ).

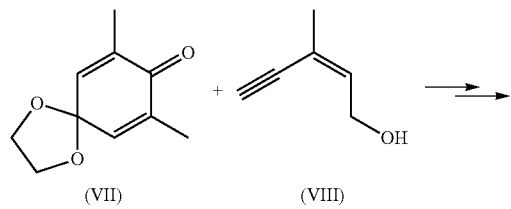

However, the enantiomer (−)-8'-acetylene ABA was shown to be biologically inactive as an agonist of ABA in studies. Therefore, the enantiomer (+)-8'-acetylene ABA is the biologically active stereoisomer (Cutler, A. J, et al. (2000) Biochemistry. 39, 13614-13624. ). Accordingly, an enantiomerically pure (+)-8'-acetylene ABA would provide a more potent form of the ABA analogue.

Accordingly, there remains a need for cost effective and efficient process for synthesis of ABA and ABA analogues, and for a process to synthesize enantiopure (+)-8'-acetylene ABA.

SUMMARY OF THE INVENTION

A method is provided for synthesis of ABA, and 8'-ABA analogues.

In accordance with a first embodiment of the invention, a method of synthesizing ABA and 8'-ABA analogues is provided wherein the previously reported first step, comprising the oxidation of 2,6-dimethylphenol (VI) to 2,6-dimethylbenzoquinone, mono ketal (VII) is replaced with a novel two step process. The first step in the process comprises oxidation of 2,6-dimethylphenol (VI) using potassium peroxymonosulfate with a catalytic amount of iodobenzene to produce 2,6-dimethylbenzoquinone (XVI).

The second step in the process provides an optimized ketalization of 2,6-dimethylbenzoquinone (XVI) using ethylene glycol, trimethylorthoformate with a catalytic amount of p-toluenesulfonic acid to produce 2,6-dimethylbenzoquinone, mono ketal (VII).

In accordance with a further embodiment of the invention, there are provided improvements in the method for synthesis of ABA and 8'-ABA analogues whereby the synthesis of quinol (XIII) from 2,6-dimethylbenzoquinone, mono ketal (VII) are carried out In only three synthetic operations in two reaction vessels with only 2 work-up procedures. These three steps require the use of reduced amount of Red-Al, specifically from two equivalents to one, and a reduced amount of total MnO$_2$, specifically from 35 equivalents to 20 equivalents as compared to the previous method. As well, these three steps are conducted at higher concentrations than used in the previous method by reducing the amount of solvents used in reactions.

In a further embodiment, the present invention provides a process for the synthesis of ABA and 8'-analogues of ABA from quinol (XIII) using an optimized Grignard step for higher yield and consistency. The process of the present invention also provides an optimized ester hydrolysis procedure.

In a preferred embodiment, the process of the invention is used to synthesize an 8'-acetylene ABA analog and an 8'-cyclopropyl ABA analogue.

The present invention also provides a process for the enantioselective conjugate addition of Grignard reagents in order to produce an enantiopure 8'-acetylene ABA analogue.

In one embodiment, the present invention provides a method of making a compound of formula 1

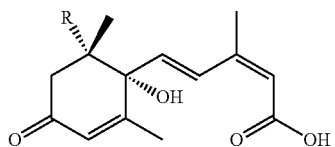

Formula 1

Wherein R is alkyl, cycloalkyl, alkenyl or alkynyl, said method comprising,
a) Reacting 2,6-dimethylphenol (VI) with potassium peroxymonosulfate and a catalytic amount of iodobenzene to produce 2,6-dimethylbenzoquinone (XVI);
b) Reacting 2,6-dimethylbenzoquinone (XVI) with ethylene glycol and a catalytic amount of p-toluenesulfonic acid to produce 2,6-dimethylbenzoquinone, mono ketal (VII);
c) Reacting 2,6-dimethylbenzoquinone, mono ketal (VII) with (Z)-3-methylpent-2-en-4-yn-4-ol (VIII), followed by reduction of the propargylic triple bond to provide allylic alcohol (X);
d) Reacting allylic alcohol (X) with MnO₂ to form aldehyde (XI) followed by addition of an organic acid and an alcohol to produce ester (XII), followed by in situ deprotection of ester (XII) in the presence of an acid to produce quinol (XIII); and
e) Reacting quinol (XIII) with a carbanion magnesium halide ((alkyl, cyloalkyl, alkenyl, or alkynyl)magnesium chloride) to produce the compound of Formula 1

In a further embodiment of the invention, there is provided, a method of making a (+)-enantiomer of a compound of formula 1

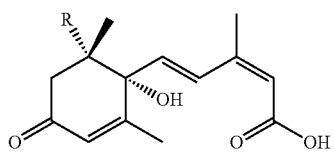

Formula 1

Wherein R is ethynyl, said method comprising,
a) Reacting 2,6-dimethylphenol (VI) with potassium peroxymonosulfate and a catalytic amount of iodobenzene to produce 2,6-dimethylbenzoquinone (XVI);
b) Reacting 2,6-dimethylbenzoquinone (XVI) with ethylene glycol and a catalytic amount of p-toluenesulfonic acid to produce 2,6-dimethylbenzoquinone, mono ketal (VII);
c) Reacting 2,6-dimethylbenzoquinone, mono ketal (VII) with (Z)-3-methylpent-2-en-4-yn-1-ol (VIII), followed by reduction of the propargylic triple bond to provide allylic alcohol (X);
d) Reacting allylic alcohol (X) with MnO₂ to form aldehyde (XI) followed by addition of an organic acid and an alcohol to produce ester (XII), followed by in situ deprotection of ester (XII) in the presence of an acid to produce quinol (XIII); and
e) Reacting quinol (XIII) with (−)-cinchonidine, with an organic or inorganic salt, water and a carbanion magnesium halide to produce the (+)-enantiomer of the compound of Formula 1

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

A method for synthesis of ABA (I), and 8'-ABA analogues, is provided which is more efficient that previously reported methods. In order to illustrate the novel method, and solely for the purpose of providing an example, descriptions are provided herein of a multigram scale production of two ABA analogues, 8'-acetylene ABA (±)-(IV) and 8'-cyclopropyl ABA (±)-(V), potent candidates for plant growth regulators. However, it will be apparent to one of skill in the art that the process of the present invention can be used to synthesize ABA and other analogues of ABA. Specific changes could include starting with a different phenol instead of 2,6-dimethylphenol (for example 2,6-diethylphenol, 2-methyl-1-naphthol or 2,6-bis(1,1-dimethylethyl)phenol). As well, removing the RedAl reduction step gives analogues containing a triple bond between C-4 and C-5. Substituting different Grignard reagents will give different 8'-analogs. For example vinylmagnesium chloride, propargylmagnesium bromide or propynylmagnesium bromide.

Several reaction sequences are carried out in a single vessel to increase the efficiency of the process as well as eliminate all purification steps requiring column chromatography. Both 8'-acetylene ABA (±)-(IV) and 8'-cyclopropyl ABA (±)-(V) have been prepared in 61% and 66% overall yield compared to 14% overall yield reported previously for 8'-acetylene ABA (±)-(IV) (see Rose, P. A.; Cutler, A. J.; Irvine, N. M.; Shaw, A. C.; Squires, T. M.; Loewen, M. K.; Abrams, S. R., *Bioorg. Med. Chem. Lett.* 1997, 7 (19), 2543-2546).

Figure 1:
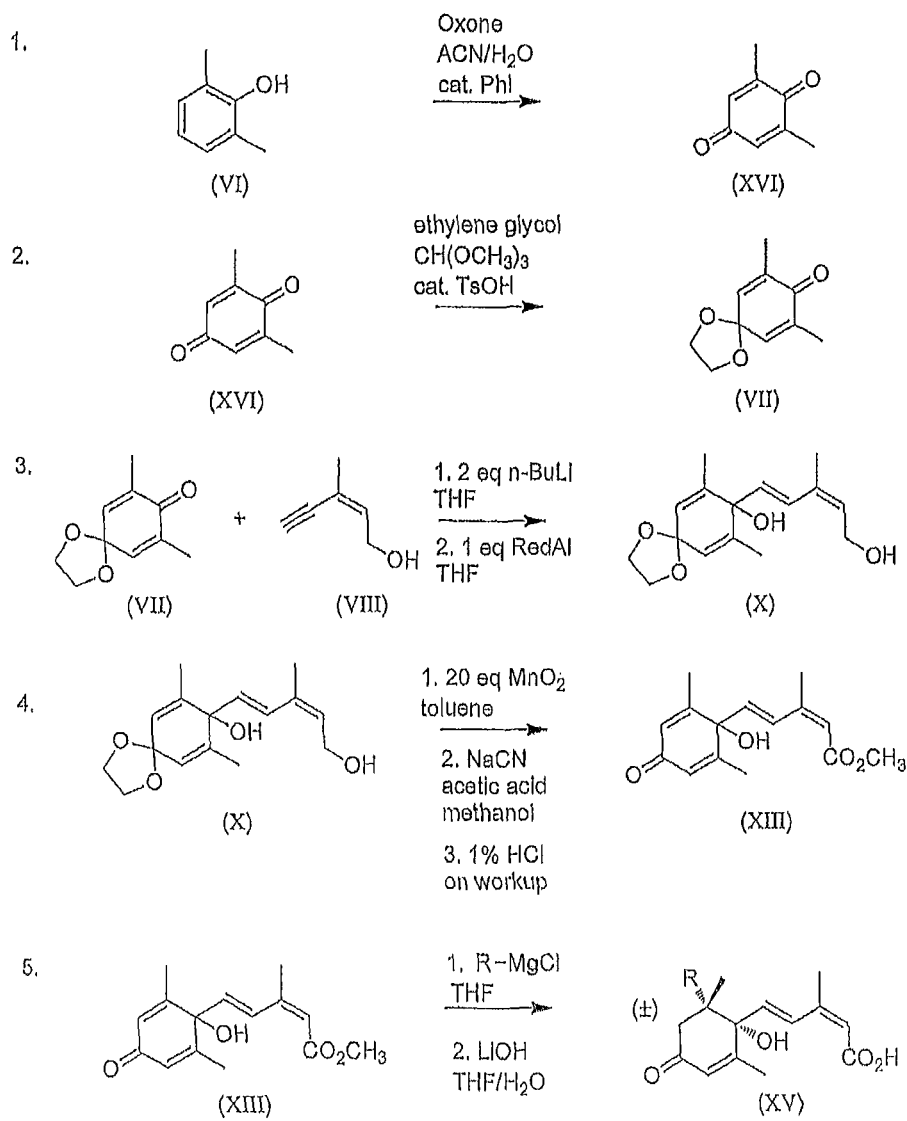
FIG. 1 illustrates the synthesis of ABA, and 8'-ABA analogues in accordance with an embodiment of the invention.

Referring to FIG. 1, the process in accordance with one embodiment of the invention is shown. As shown in FIG. 1, the previously reported first step, comprising the oxidation of 2,6-dimethylphenol (VI) to 2,6-dimethylbenzoquinone, mono ketal (VII), is replaced with a novel two step process. The first step of the process of the Invention consists of oxidizing 2,6-dimethylphenol (VI) to 2,6-dimethyl-1,4-benzoquinone (XVI). Synthesis of the ketal (VII) is effected in an improved second, separate step. It has been observed that utilization of the two novel steps results in fewer byproducts and the desired products are easily purified by recrystallization.

There are several examples of the oxidation of 2,6-dimethylphenol (VI) to 2,6-dimethyl-1,4-benzoquinone (XVI) in the literature (for example, Minisci, F.; Citterio, A,; Vismara, E.; Fontana, F.; De Bernardinis, S.; Correale, M., *The Journal of Organic Chemistry* 1989, 54 (3), 728-731. ) Traditional synthetic methods to oxidize phenols involved catalytic amounts of transition metals, a co-oxidant (usually a peroxide) and a strong acidic medium. These methods present a problem for the large scale synthesis of 2,6-dimethyl-1,4-benzoquinone (XVI) because of the difficult work-up involved or the use of potentially explosive reagents. Another strategy involves coupling the phenol with diazotized sulfanilic acid followed by a reduction and an oxidation step (Sakaino, M.; Meinwald, J., *Tetrahedron Letters* 1987, 28 (28), 3201-3204). This procedure involves more reagents and has more steps which adds to the cost. It also calls for stannous chloride which undesirable for environmental reasons. Alternatively, hypervalent iodine reagents have been used to oxidize para-substituted phenols and phenol ether derivative's to quinones (Tohma, H.; Morioka, H.; Harayama, Y.; Hashizume, M.; Kita, Y., *Tetrahedron Lett.* 2001, 42 (39), 6899-6902). However, the reagent used in this process is too expensive for use on an industrial scale.

Recently, a catalytic oxidation of p-alkoxyphenols to p-benzoquinones using potassium peroxymonosulfate, an oxidizing agent sold in association with the trade-mark Oxone®, and an aryl iodide has been reported (Yakura, T.; Tian, Y.; Yamauchi, Y.; Omoto, M.; Konishi, T., *Chem. Pharm. Bull.* 2009, 57 (3), 252-256. ). The rearrangement and oxidation, in a non-catalytic reaction, of arylcarboamides to p-benzoquinones using similar conditions has also been reported (Zagulyaeva, A. A.; Banek, C. T.; Yusubov, M. S.; Zhdankin, V. V., *Organic Letters* 2010, 12 (20), 4644-4647).

Different protocols were used to effect the oxidation of 2,6-dimethylphenol (VI) to 2,6-dimethyl-1,4-benzoquinone (XVI). Due to the mild and inexpensive reaction conditions, oxidation of 2,6-dimethylphenol (VI) to 2,6-dimethyl-1,4-benzoquinone (XVI) using in situ generated hypervalent iodine was studied as shown below. The reaction conditions were optimized for temperature, solvent and aryl iodide (ArI) catalyst. The preferred conditions for the oxidation of 2,6-dimethylphenol (VI) to 2,6-dimethyl-1,4-benzoquinone (XVI) was addition of 3 mole equivalents potassium peroxymonosulfate and 0.1 mole equivalents Iodobenzene in acetonitrile/water (1:2 v/v) at 40 to 50° C.

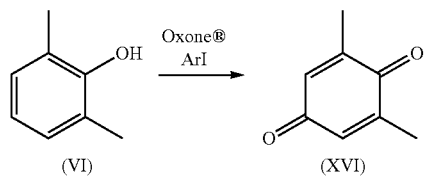

The procedure described by Yakura et al. was also used. Initial experiments using the procedure described by Yakura at al, for the oxidation of p-alkoxyphenols were able to oxidize (VI) to (XVI) in 2,2,2-trifluoroethanol (TFE)-H$_2$O (1:2) at room temperature. This process used 4 equivalents of potassium peroxymonosulfate and 0.05 equivalents of 4-iodophenoxyacetic acid (IPAA) and it oxidized (VI) to (XVI) in. 3 hours. The conversion was nearly quantitative, as monitored by gas chromatography, and the isolated yield was 60%. The reaction also produced a dark green colored impurity that prevented easy purification.

In order to find reaction conditions better suited for 2,6-dimethylphenol (VI), optimization of the reaction conditions was carried out. The results of the optimization experiments are summarized In Table 1. Reducing the amount of potassium peroxymonosulfate or changing the amount of catalyst did not reduce the formation of byproducts (see Table 1, entries 1-5). Substituting the catalyst for either 2-iodobenzoic acid (IBA) or o-iodoxybenzoic acid (IBX) gave a lower conversion of (VI) to (XVI). Iodobenzene (PhI), entry 8 in Table 1, showed good catalytic behavior but also produced highly colored impurities in TFE-H$_2$O. A number of solvents were screened, (see Table 1, entries 9-14) and acetonitrile-H$_2$O (1:2 v/v) was found to provide high conversion of (VI) to (XVI) with few byproducts. The oxidation was performed on a phenol that lacked functionality para to the hydroxyl group, unlike previous literature examples.

TABLE 1

Optimization of the Oxidation of 2,6-Dimethylphenol (VI) to 2,6-Dimethyl-1,4-benzoquinone (XVI).

| Entry | Catalyst (mole eq) | Oxone (mole eq) | Solvent (ratio v/v) | Conv. (% GC) |
|---|---|---|---|---|
| 1 | IPAA (0.05) | 4 | TFE-H$_2$O (1:2) | 99 |
| 2 | IPAA (0.05) | 2 | TFE-H$_2$O (1:2) | 82 |
| 3 | IPAA (0.05) | 1 | TFE-H$_2$O (1:2) | 41 |
| 4 | IPAA (0.1) | 4 | TFE-H$_2$O (1:2) | 99 |
| 5 | IPAA (0.01) | 4 | TFE-H$_2$O (1:2) | 67 |
| 6 | IBA$^a$ (0.05) | 4 | TFE-H$_2$O (1:2) | 75 |
| 7 | IBX$^b$ (0.05) | 4 | TFE-H$_2$O (1:2) | 77 |
| 8 | PhI (0.05) | 4 | TFE-H$_2$O (1:2) | 97 |
| 9 | IPAA (0.05) | 1 | ethanol-H$_2$O (1:2) | 89 |
| 10 | IPAA (0.05) | 4 | CH$_3$CN—H$_2$O (2:1) | 48 |
| 11 | IPAA (0.05) | 4 | CH$_3$CN—H$_2$O (1:2) | 97 |
| 12 | IPAA (0.05) | 4 | TFE-H$_2$O (2:1) | 10 |
| 13 | IPAA (0.05) | 4 | acetone-H$_2$O (1:2) | 27 |
| 14 | IPAA (0.05) | 4 | ethylene glycol/ hexanes (1:1) | 99 |

$^a$2-Iodobenzoic acid;
$^b$o-iodoxybenzoic acid.

In further experiments to optimize the process, iodobenzene (PhI) was used instead of IPAA as the catalyst. IPAA was developed as a recyclable catalyst; however it costs significantly more than PhI. Oxidation of 2,6-dimethylphenol (VI) in acetonitrile-H$_2$O (1:2 v/v) at 50° C. using potassium peroxymonosulfate (5 eq) and PhI (0.1 eq) was complete in 3 hours. The work up was straightforward and simple. First, the potassium salts from the potassium peroxymonosulfate were filtered off using a glass sintered funnel and the aqueous layer extracted with hexanes/diethyl ether (9:1 v/v). 2,6-Dimethylbenzoquinone (XVI) was isolated in 63% yield as a bright yellow solid and was further purified by recrystallization from pentane. 2,6-Dimethylbenzoquinone (XVI) can also be carried forward to the ketallization step without any purification.

Two prior art procedures for the monoketallization of 2,6-dimethylbenzoquinone (XVI) to 2,6-dimethylbenzoquinone, mono ketal (VII) give limited details for this transformation (Sakaino, M.; Meinwald, J., *Tetrahedron Lett,* 1987, 28 (28), 3201-3204 and Frank-Neumann, M.; Miesch, M.; Barth, F., *Tetrahedron Lett.* 1989, 30 (27), 3537-3540. ). Sakaino and Meinwald used ethylene glycol, p-toluenesulfonic acid (TsOH) and trimethylorthoformate to convert (XVI) to (VII). No reaction conditions regarding solvent, temperature or reaction time were given. Frank-Neuman, at al. used the same reagents but indicated that the reaction was run in benzene at 25° C. for 24 hours. It was found that 2,6-dimethylbenzoquinone (XVI) undergoes side reactions during the ketallization step that negatively affects the alkylation of 2,6-dimethylbenzoquinone, mono ketal (VII) with (Z)-3-methylpent-2-en-4-yn-1-ol (VIII) (leading to lower yields and chemical purity). Therefore, reaction conditions were optimized to limit side product formation using the following conditions:

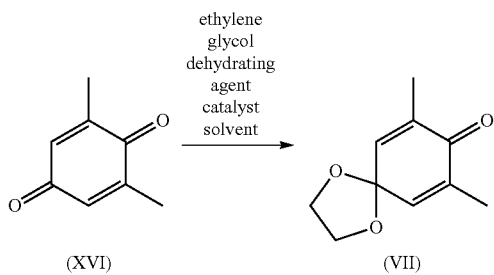

This optimization process was also directed to finding reaction conditions better suited for monoketallization of 2,6-dimethylbenzoquinone (XVI). The results of the optimization experiments are summarized in Table 2.

TABLE 2

Optimization of the Conversion of 2,6-Dimethylbenzoquinone (XVI) to 2,6-Dimethylbenzoquinone, mono ketal (VII).

| Entry | Catalyst | Dehydrating agent | Solvent | Ratio XVI:VII[a] (by GC) | Purity[b] (%) |
|---|---|---|---|---|---|
| 1 | TsOH | HC(OMe)$_3$ | acetonitrile | 1:15 | 41[c] |
| 2 | TsOH | HC(OMe)$_3$ | dichloromethane | 1:33 | 49[c] |
| 3 | TsOH | HC(OMe)$_3$ | tetrahydrofuran | 23:1 | 3 |
| 4 | TsOH | HC(OMe)$_3$ | benzene | 1:19 | 56[c] |
| 5 | TsOH | HC(OMe)$_3$ | toluene | 1:26 | 45[c] |
| 6 | TsOH | HC(OMe)$_3$ | 1,4-dioxane | 13:1 | 6 |
| 8 | TsOH | CaSO$_4$ | HC(OMe)$_3$ | 3:1 | 10 |
| 9 | TsOH | HC(OMe)$_3$ | ethylene glycol | 1:6 | >95 |
| 10 | TsOH | CaSO$_4$ | dichloromethane | 11:1 | >95 |
| 12 | TsOH | Na$_2$SO$_4$ | dichloromethane | no reaction | |
| 13 | TsOH | MgSO$_4$ | dichloromethane | no reaction | |
| 14 | Amberlyst 15 | HC(OMe)$_3$ | dichloromethane | 1:1 | >95 |
| 15 | DOWEX 50WX2 | HC(OMe)$_3$ | dichloromethane | no reaction | |
| 16 | Amberlyst 15 | HC(OMe)$_3$ | acetonitrile | 1:5 | 72[c] |
| 17 | DOWEX 50WX2 | HC(OMe)$_3$ | acetonitrile | no reaction | |
| 18 | Amberlyst 15 | CaSO$_4$ | dichloromethane | no reaction | |
| 19 | Amberlyst 15 | CaSO$_4$ | acetonitrile | 17:1 | >95 |
| 20 | Amberlyst 15 | CaSO$_4$ | ethylene glycol | 19:1 | >95 |

[a]Ratio of starting material to product after 5 h.
[b]Estimate of product purity determined as a percentage of all peaks (excluding unreacted starting material) detectable by gas chromatography after 5 h.
[c]Significant decomposition after 24 h.

Referring to Table 2, the ketal formation was highly sensitive to the solvent used. The preferred conditions (entry 9) were found to be the standard reagents (ethylene glycol, trimethylorthoformate and TsOH catalyst) but with no additional solvent. Eliminating the reaction solvent significantly improved the product yield and purity.

The preferred ketalization conditions were to dissolve 2,6-dimethylbenzoquinone (XVI) in (MeO)$_3$CH, heat to 40° C. and add ethylene glycol. When the internal temperature has reached 40° C., the catalyst (0.1 mole equivalents TsOH) is added. It is stirred for 1 to 2 h and monitored by gas chromatography (GC). 2,6-Dimethylbenzoquinone (XVI) was converted to 2,6-dimethylbenzoquinone, mono ketal (VII) in 90% yield using these conditions.

Following optimization of the first and second steps of the process, experiments were conducted to reduce the number of steps In the reminder of the synthesis.

Referring to FIG. 1, experiments were conducted to merge the alkylation of 2,6-dimethylbenzoquinone, mono ketal (VII) with (Z)-3-methylpent-2-en-4-yn-1-ol (VIII) followed by a reduction of the propargylic triple bond with Red-Al to provide allylic alcohol (X) in a sequential fashion employing the following specific conditions. To a solution of (Z)-3-methylpent-2-en-4-yn-1-ol (VIII) in tetrahydrofuran (THF), 2 mole equivalents of n-butyl lithium was slowly added. After 4-5 hours at −78° C., a solution of ketone (VII) in THF was added at −78° C. followed by prolonged stirring at −20° C. overnight. After all ketone (VII) had reacted, 1 mole equivalent RedAl was added dropwise via a syringe pump to intermediate (XVII) at −20° C. for 3 hours. The alkylated intermediate (X), shown below, was obtained at greater than 98% conversion from (WI) (>95% purity as determined by $^1$H NMR).

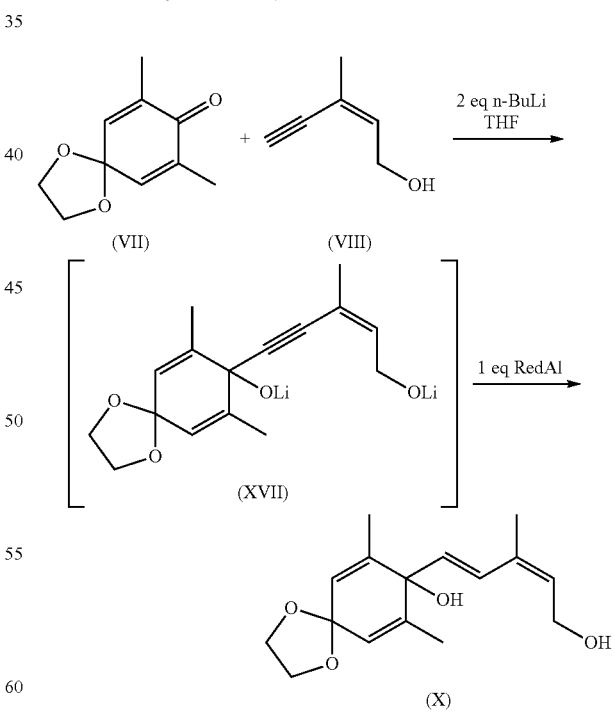

Intermediate (XVII) was not isolated. Once full conversion of mono ketal (VII) to intermediate (XVII) was confirmed by $^1$H NMR, 1 equivalent of Red-Al (or 2 mole equivalents of hydride) was slowly added to the reaction mixture at an internal temperature of between −20 and 0° C.

Alkyne reduction produced alcohol (X) as the sole product in a very high crude yield (90-95% purity by $^1$H NMR). The purity of crude alcohol (X) was improved when ice cooled tartrate solution (Rochelle's salt) was used in the work up procedure. Careful monitoring of temperature during reaction and work up was important as was avoiding the use of magnesium sulfate as a drying agent. This reaction sequence was reproduced on 20 g to 100 g scales. By combining the alkylation and reduction steps, the amount of solvent and Red-Al required was reduced and a work up step was eliminated.

The improved efficiency of conversion of alcohol (X) to quinol (XIII) was accomplished by combining the two oxidation steps into a single pot and removing the ketal protecting group during the reaction work-up. In previous ABA syntheses (Lei, at al, (1994) *Phytochem,* 37, 289-296.), three distinct steps were required to produce quinol (XIII) from alcohol (X): (a) oxidation of an allylic alcohol to an aldehyde employing $MnO_2$, (b) conversion of the resultant aldehyde to its methyl ester using Corey's protocol (Corey, E. J.; Gilman, N. W.; Ganem, B. E., *Journal of the American Chemical Society* 1968, 90 (20), 5616-5617) and, (c) deketalization under acidic conditions (Rose, P. A.; Lei, B.; Shaw, A. C.; Walker-Simmons, M. K.; Napper, S.; Quail, J. W.; Abrams, S. R., *Canadian Journal of Chemistry* 1996, 74 (10), 1836-1843. ). The previous process required three different solvents, three reaction work-ups and three evaporation steps to effect the conversion of alcohol (X) to quinol (XIII).

The prior art procedure (Lei, et al. (1994) Phytochem. 37, 289-296) used acetone as solvent for the first oxidation to the aldehyde and then methanol as the solvent for the second oxidation to convert the resulting aldehyde to its methyl ester. It was not known if both oxidation steps could be carried out in a single solvent or mixture of solvents. Experiments showed that the two oxidation steps did not proceed satisfactorily in THF, methanol, acetone, dichloromethane or a 1:1 mixture of toluene and THF. However, using toluene, the reaction proceeded smoothly with excellent conversion, as determined by $^1$H NMR, with a negligible amount of decomposition and double bond isomerization.

A sequential oxidation process to convert the alcohol (X) to ester (XII) was developed in a single reaction vessel. The development of the sequential oxidation process is illustrated below.

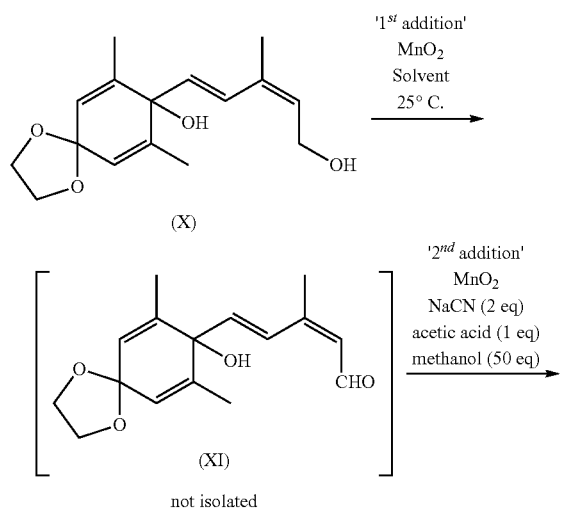

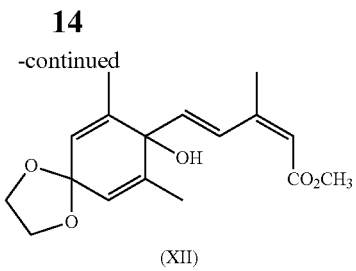

As is shown, aldehyde (XI) is formed from alcohol (X) by a 1st addition of $MnO_2$ followed by a 2nd addition of $MnO_2$ accompanied by sodium cyanide (2 eq), acetic acid (1 eq) and methanol (50 eq). The first and second additions are effected in the same reaction vessel to produce ester (XII). Various conditions were tried in order to optimize this sequential process and the results are summarized in Table 3.

TABLE 3

Optimization Conditions for the Sequential Oxidation of Alcohol (X) to Aldehyde (XI) and then to Ester (XII)

| Entry | Solvent | 1st add'n $MnO_2$ (eq) | Conv. to (XI) (%) (5 h) | 2nd add'n $MnO_2$ (eq) | Conv. to (XII) (%) (16 h) | (48 h) |
|---|---|---|---|---|---|---|
| 1 | toluene | 5 | 20 | 10 | 30 | Not determined |
| 2 | toluene | 10 | 46 | 10 | 52 | Not determined |
| 3 | toluene | 15 | 80 | 10 | 45 | Not determined |
| 4 | toluene | 15 | 80 | 0 | 68 | 76 |
| 5 | toluene | 20 | 95 | 0 | 73 | 96 |
| 6 | toluene | 25 | 98 | 0 | 92 | 100 |
| 7 | THF | 10 | 54 | 10 | 22 | Not determined |
| 8 | THF | 15 | 80 | 10 | 30 | Not determined |

All reactions were carried out at room temperature on a 0.4 mmol scale with a concentration of 0.25 M with respect to alcohol (X). The solvents used were anhydrous solvents. The first addition of $MnO_2$ was used to convert alcohol (X) to intermediate (XI). The second addition of $MnO_2$ was used to convert intermediate (XI) to ester (XII). No second addition of $MnO_2$ was used for entries 4, 5 and 6. Conversion was determined by $^1$H NMR of the crude reaction mixture.

The results in Table 3 show that it is important to allow full conversion of the alcohol (X) to the intermediate (XI) before adding the second set of reagents in order to achieve a better yield of ester (XII) (See Table 3, entries 5 and 6). It was also observed that the reaction considerably slowed after the second addition of reagents (without allowing full conversion of alcohol (X) to intermediate (XI) after the first addition) even though the net amount of $MnO_2$ introduced at the end of the process is the same when comparing entries 2 and 3 with 5 and 6 in Table 3. Employing 20-25 equivalents of $MnO_2$ in the 1st addition proved sufficient to promote both oxidative steps. The workup required a simple filtration to remove $MnO_2$ and then treatment of the resulting filtrate with 1% ice cooled hydrochloric acid. This reaction produced quinol (XIII) in 80-84% yield in five steps (two single vessel reactions) from starting ketone (VII). The sequence proved to be reproducible on a large scale (32 g) employing conditions in Table 3, entry 6. Quinol (XIII) can be used as the direct precursor for the synthesis of ABA and 8'-ABA analogs (Abrams, et al. (1997) *Plant Physiol* 114, 89-97; Rose at al. (1997) *Bioorg. Med. Chem. Lett.* 7, 2543-2546.; Abrams, et al. (2003) *J. Label. Compd. Radiopharm.* 46, 273-28 3). The synthesis of the end product ABA or 8'-ABA analog is conducted by the 1,4-conjugate addition of a carbanion magnesium halide followed by base catalyzed hydrolysis of the methyl ester. Suitable carbanion magnesium halides include alkyl, cycloalkyl, alkenyl or alkynyl magnesium chloride. Alkyl, alkenyl and alkynyl groups can have from 1 to 12 carbon atoms while cycloalkyl groups can have from 3 to 8 carbon atoms. Particularly preferred carbanion magnesium halide compounds include ethynylmagnesium chloride, ethynylmagnesium bromide, vinylmagnesium chloride, vinylmagnesium bromide, cyclopropylmagnesium chloride or cyclopropylmagnesium bromide. The synthesis of end product racemic ABA is achieved by the 1,4-conjugate addition of methylmagnesium bromide or methylmagnesium chloride with quinol (XIII), followed by base catalysized hydrolysis of the methyl ester.

Having developed a protocol to produce quinol (XII) on a multi gram scale, the next step in the process which was optimized was the conjugate addition of an ethynyl or cyclopropyl group to quinol (XII) en route to 8'-acetylene ABA (±)-(IV) and 8'-cyclopropyl ABA (±)-(V).

The regioselective conjugate addition of ethynylmagnesium bromide to quinol (XIII) producing a single diastereomer of methyl 8'-acetylene ABA (XVIII) as shown below has been previously reported (Rose at al. (1997) *Bioorg. Med. Chem. Lett.* 7, 2543-2546. ).

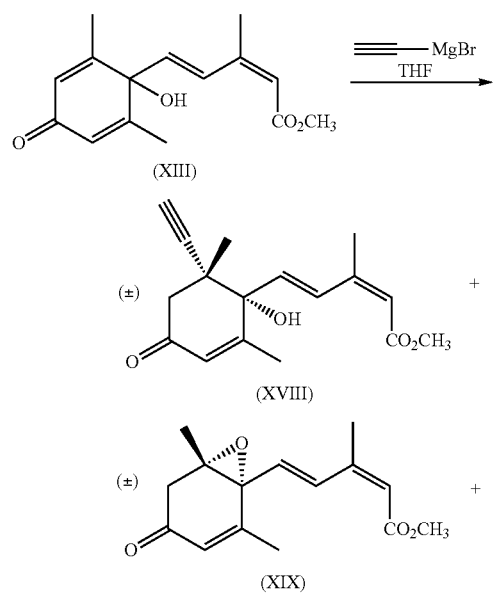

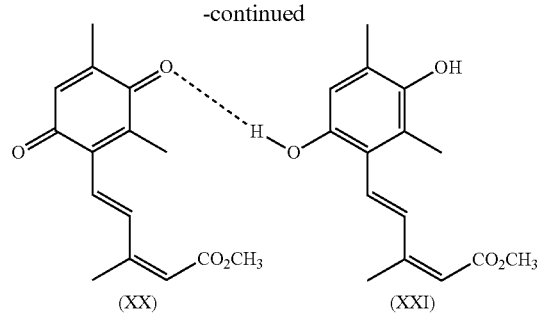

Optimization of the 1,4-conjugate addition reaction using ethynyl Grignard reagent was investigated. The mechanism for this type of reaction is referred to as ligand assisted nucleophilic addition (LANA). (Solomon, M.; Jamison, W. C. L.; McCormick, M.; Liotta, D.; Cherry, D. A.; Mills, J. E.; Shah, R, D.; Rodgers, J. D.; Maryanoff, C. A, Journal of the American Chemical Society 1988, 110 (11), 3702-4. ) The aim was to minimize side products which include epoxide (XIX) and a third unknown component (ca. 30%) that was isolated as black (very dark red) crystals. These crystals were later characterized to be quinhydrone (XX:XXI), after recrystallization of the mother liquor containing a substantial amount of methyl 8'-acetylene ABA (±)-(XVIII) from 1:1 benzene/hexane. It is possible that the hydroquinone (XXI) was produced during the reaction and subsequently oxidized to quinone (XX) (as a bright yellow oil) during purification, and the two compounds crystallized as a 1:1 mixture to the quinhydrone (XX:XXI). X-ray crystallography confirmed the structure to be a quinhydrone comprising a 1:1 mixture of hydroquinone (XXI) and quinone (XX).

The reaction conditions were optimized for the conjugate addition of ethynyl Grignard reagents to quinol (XIII). A THF solution of quinol (XIII) was slowly added over a range of conditions to cooled Grignard reagents and their conversions were measured after 24 hours. The results of these experiments are summarized in Table 4.

TABLE 4

Conjugate addition of Grignard reagents to quinol (XIII) to produce methyl 8'-acetylene ABA (±)-(XVIII).

| Entry | ethynylMgX | Equiv. | Temp. (° C.) | Conv. XVIII (%) |
|---|---|---|---|---|
| 1 | X = Br | 2 | −20 | <20 |
| 2 | X = Br | 3 | −20 | 66 |
| 3 | X = Br | 5 | −20 | 75 |
| 4 | X = Br | 7.5 | −20 | 80 |
| 5 | X = Br | 10 | −20 | 85 |
| 6 | X = Br | 5 | −78 | No reaction |
| 7 | X = Br | 5 | −10 | 95 |
| 8 | X = Cl | 5 | −10 | 99 |

All experiments shown in Table 4 were carried out in 0.4 mmol scale, 0.5 M ethynylmagnesium halide reagent and conversions were measured after 24 hours. The % conversion shown in Table 4 was determined by $^1$H NMR of the crude reaction mixture. In entry 1, a complex mixture was observed with hydroquinone (XXI) (ca. 50%) accompanied by unreacted quinol (XIII) (ca. 30%) and >10% of product (±)-(XVIII) and epoxide (XIX). However, using less reactive ethynylmagnesium chloride instead of ethynylmagnesium bromide (entry 9), excellent conversion and purity (>95%) of crude product (±)-(XVIII) was obtained as determined by $^1$H NMR. The set of conditions in entry 8 were therefore preferred and proved consistent during scale up.

As a trend, when the proportion of ethynylmagnesium bromide was increased, conversion improved significantly and the amount of side products epoxide (XIX) and hydroquinone (XXI) were substantially reduced, with unreacted quinol (XIII) recovered intact (see Table 4, entries 1-5). Optimal conversion was observed at −10° C. (see Table 4, entries 7 and 8). Scaled up conditions using ethynylmagnesium bromide (see Table 4, entry 7) resulted in the formation of substantial amounts of epoxide (XIX) and hydroquinone (XXI). However, repeating the reaction using ethynylmagnesium chloride on a 15 g scale (i.e. conditions of entry 8) was successful, producing desired methyl 8'-acetylene ABA (±)-(XVIII) in 87-98% crude yields with >90% purity (by $^1$H NMR). Target product 8'-acetylene ABA (±)-(IV) was achieved in >75% yield via hydrolysis of methyl 8'-acetylene ABA (±)-(XVIII) using LiOH/THF (1:1).

An 8'-cyclopropyl ABA (±)-(V) analogue was synthesized using the process of the invention. Addition of a THF solution of quinol (XIII) to freshly prepared cyclopropylmagnesium bromide in the presence of trimethylsilyl chloride at −78° C. produced the corresponding 1,4-adduct (methyl-8'-cyclopropyl ABA) as the sole diastereomer. This was then followed by ester hydrolysis to furnish 8'-cyclopropyl ABA (±)-(V) in 79% yield over 2 steps. Methyl 8'-cyclopropyl and 8'-cyclopropyl ABA (±)-(V) have a propensity to easily precipitate out of solution (1:1 hexane/ether), thereby providing a practical method for purification using filtration.

Figure 2:
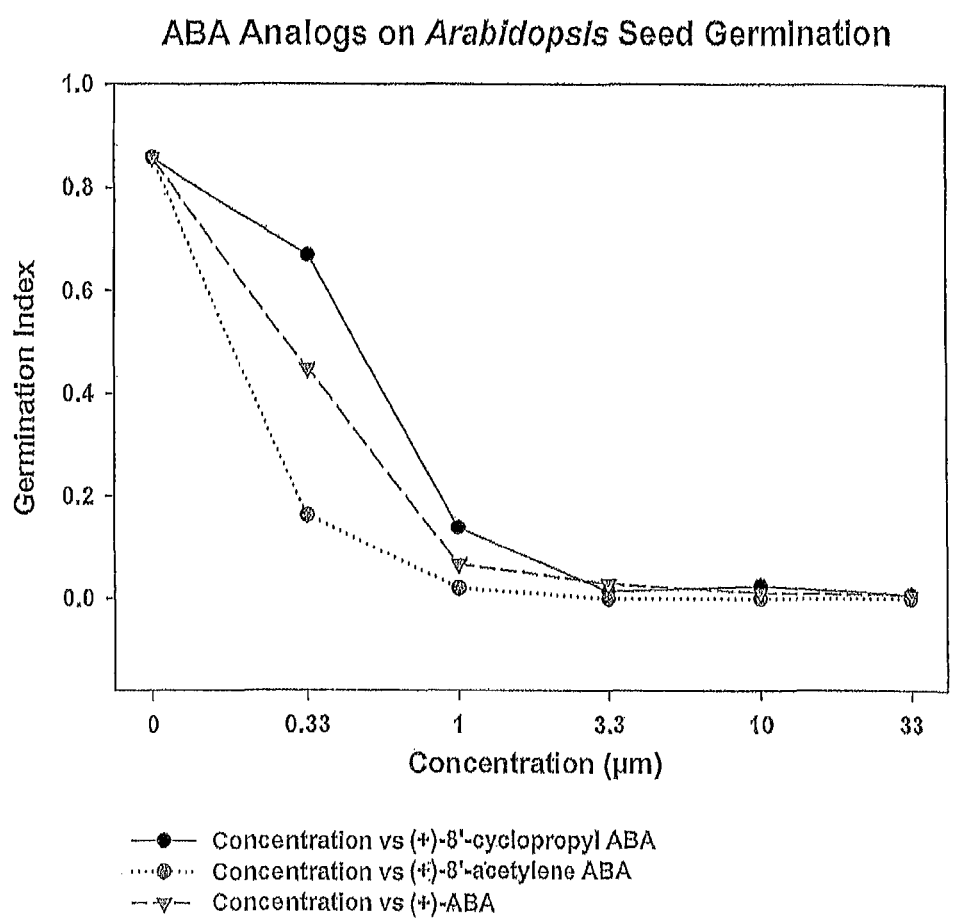
FIG. 2 is a graph illustrating germination index versus concentration for *Arabidopsis* seeds treated with (+)-ABA (I), (+)-8'-acetylene ABA (+)-(IV) and (+)-8'-cyclopropyl ABA (+)-(V)

The effect of (+)-ABA (I), and analogs (+)-8'-acetylene ABA (+)-(IV) and (+)-8'-cyclopropyl ABA (+)-(V) on *Arabidopsis* seed germination was studied. The results are shown in FIG. 2. A weighted germination index in which seeds that germinate first are given more weight was calculated for each compound at varying concentrations (Walker-Simmons, M., *Plant, Cell and Environment* 1988, 11 (8), 769-75. ) 8'-Cyclopropyl ABA (±)-(V) shows strong, although slightly weaker ABA activity in this assay. However, 8'-cyclopropyl ABA (±)-(V) may be easier to produce on a commercial scale than 8'-acetylene ABA (±)-(IV) making it a more attractive plant growth regulator for commercial use.

Figure 3:
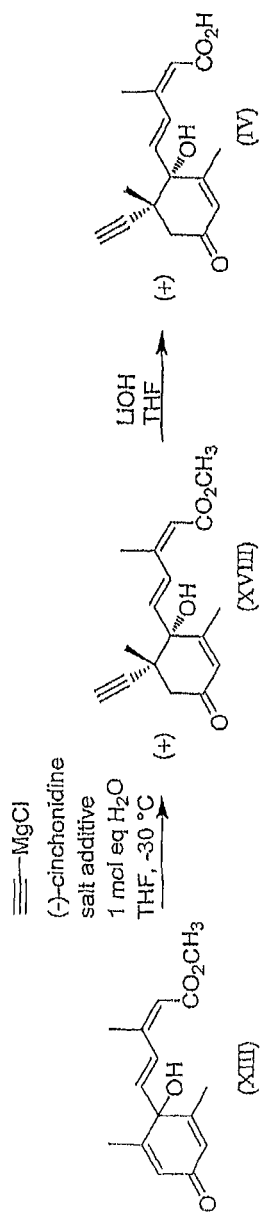
FIG. 3 illustrates a process for enantioselective synthesis of (+)-8'-acetylene ABA (+)-(IV).

A further goal of the present invention is to synthesize enantiomerically pure (+)-8'-acetylene ABA (+)-(IV), which is the biologically active form. Based on the protocol described above to produce a racemic mixture of 8'-acetylene ABA (IV), enantioselective conjugate addition (ECA) of an ethynyl nucleophile to the 4,4-disubstituted-3,5-dimethylcyclohexadienone (p-quinol) intermediate (XIII) was investigated as a direct route to produce (+)-8'-acetylene ABA (+)-(IV) (see FIG. 3). There have been major advancements in asymmetric conjugate alkylation, arylation and alkenylation by employing transition metal reagents (see Krause, N. *Modern Organocopper Chemistry*; Wiley-VCH Verlag GmbH: Weinheim, Germany, 2002). However, performing an asymmetric conjugate alkynylation on the p-quinol intermediate (XIII) poses several concerns. Firstly, only a few reports have been published on enantioselective conjugate alkynylation (see for example, Fujimori, S.; Knoepfel, T. F.; Zarotti, P.; Ichikawa, T.; Boyall, D.; Carreira, E. M. *Bull. Chem. Soc. Jpn*, 2007, 80, 1635) and these reports have described serious substrate scope limitations. There have been few reports of ECA on 4,4-disubstituted cyclohexadienones (for example, Imbos, R.; Minnaard, A. J.; Feringa, B. L. *Tetrahedron* 2001, 57, 2485) and generation of all carbon quaternary centers (see, for example, Hawner, C.; Alexakis, A. *Chem, Commun.* 2010, 46, 7295) via ECA.

As a further challenge, desymmetrization and diastereofacial selectivity of symmetrical 4,4-disubstituted cyclohexadienones can generate up to four stereoisomers (see Merino, E.; Melo, Rosanne P. A.; Ortega-Guerra, M.; Ribagorda, M.; Carreno, M. C. *J. Org. Chem.* 2009, 74, 2824). Difficulty can also be encountered in effecting regioselective conjugate addition on the p-quinol template of (XIII) without resulting in any 1,4-insertion to the α,β-unsaturated ester moiety of the side chain.

Grignard reagents were used rather than transition metals because quinol (XIII) is susceptible to rearrangement or decomposition upon exposure to transition metals under certain conditions. Also, the alkynyl nucleophile is inert in copper-catalyzed conjugate additions due to strong binding affinity with copper metal. Acceptable levels of enantioselectivity in asymmetric conjugate addition using Grignard reagents have only been observed when a catalytic amount of copper salts were added in the presence of the chiral catalyst (see Harutyunyan, S. R.; Den Hartog, T.; Geurts, K.; Minnaard, A. J.; Feringa, B. L. Chem. Rev. 2008, 108, 2824-2852).

Based on the aforementioned considerations, ECA using Grignard reagents without the introduction of any Cu(I) salts or any other transition metals was developed for asymmetric conjugate addition of ethynylmagnesium chloride to an advanced p-quinol (XIII) en route to the synthesis of (+)-8'-acetylene ABA (+)-(IV) in the absence of transition metals.

Prior art of the enantioselective conjugate alkynylation of Meldrum's acid using a stoichiometric amount of (−)-cinchonidine as a chiral ligand in the presence of ZnMe$_2$ was described by Shen Cui et al (Cui, S.; Walker, S. D.; Woo, J. C. S.; Borths, C. J.; Mukherjee, H.; Chen, M. J.; Faul, M. M. *J. Am. Chem. Soc.* 2010, 132, 436). Using a modified procedure, quinol (XIII) was reacted with 5 eq of (−)-cinchonidine and 10 eq of ethynylMgCl in the absence of ZnEt$_2$ and valeric acid at −25° C. This reaction furnished the desired product as a single diastereomer in >80% conversion and 34% enantiomeric excess (ee). No reaction was observed when ZnEt$_2$ and valeric acid were included at either −25° C. or 0° C. Several other reaction parameters were tested and the results are summarized in Table 5.

TABLE 5

Investigation of Reaction Parameters for the Enantioselective Synthesis of (+)-Methyl 8'-acetylene ABA ester (+)-(XVIII)

| Entry | (−)-Cinchonidine (eq) | Time (days) | Temp. (° C.) | ethynylMgCl (eq) | Conv. (%) | ee (%) |
|---|---|---|---|---|---|---|
| 1 | 2.5 | 3 | −25 | 7.5 | 80 | 40 |
| 2 | 5 | 3 | −25 | 10 | 80 | 34 |
| 3 | 7.5 | 3 | −25 | 12.5 | 80 | 34 |
| 4 | 2.5 | 2.5 | −35 | 7.5 | >95 | 49 |
| 5 | 1.25 | 2.5 | −35 | 6.25 | >95 | 42 |
| 6 | 0.65 | 2.5 | −35 | 5.65 | >95 | 35 |
| 7 | 2.5 | 2.5 | −35 | 3.5 | decomposed | |
| 8 | 2.5 | 2.5 | −35 | 5.5 | <20 | 41 |
| 9 | 2.5 | 2.5 | −35 | 7.5 | <20 | 9 |
| 10 | 2.5 | 2.5 | −50 | 7.5 | 41 | 51 |
| 11 | 2.5 | 2.5 | −50 | 9.5 | 28 | 50 |
| 12 | 2.5 | 2.5 | −50 | 11.5 | 22 | 46 |

The conversions shown in Table 5 were measured directly from HPLC data. All ee measurements were measure by chiral HPLC using a (R,R)-Whelk O1 column, 1.5 mL/min, hexanes: IPA=92:8 at room temperature. The ee was calculated as the difference of the peak areas corresponding to the (+)- and (−)-enantiomers divided by the sum of the peak areas corresponding to the (+)- and (−)-enantiomers then multiplied by 100. For entry 9, ethynylMgBr was used instead of ethynylMgCl.

The ee of the reaction was found to be sensitive to the relative amount of ligand added (see entries 1-3, Table 5). Higher loading of (−)-cinchonidine produced the desired product in lower ee, although an excess of 5 eq of ethynylMgCl was maintained in all three experiments. When the conditions of entry 1 were repeated at −35° C. (entry 3), a significant increase in ee (49%) and conversion (>95%) were noted. A lower loading of ligand did not improve the reaction (see entries 5 and 6). Keeping the conditions of entry 4 as a control, it was observed that both yields and ee's suffered when the net amount of unreacted ethynylMgCl was reduced from 5 to 1 eq (entries 7 and 8). Although, ee was somewhat better at −50° C., however, conversions were poor (entries 10-12). It is noteworthy that conversion and enantioselectivity greatly diminished, when the halide ion of the Grignard reagent was switched to bromide (see entry 9). Therefore, ethynylmagnesium chloride was preferred for further screening.

Different ligands were screened to compare their performance to (−)-cinchonidine. The results are shown in Table 6. None of the different ligands tested provided better results than (−)-cinchonidine. Quinidine derived ligands, structurally similar to (−)-cinchonidine, offered slightly lower ee than (−)-cinchonidine. Interestingly, (S,S)-chiraphos, quinidine, dihydroquinidine and (−)-N-methylephedrine ligands produced the (−)-enantiomer of methyl 8'-acetylene ABA ester (XVIII) instead of the (+)-enantiomer (see entries 4, 7, 8 and 9). Accordingly, these ligands can be used to produce the (−)-enantiomer if required. The screening results are shown in Table 6. The net amount of unreacted ethynylMgCl in each reaction after mixing the ligand with ethynylMgCl was calculated to be 5 equivalents.

TABLE 6

Screening of Ligands for the Enantioselective Synthesis of (+)-Methyl 8'-acetylene ABA ester (XVIII)

| Entries | Ligands (2.5 eq) | EthynylMgCl (eq) | Conversions (%) | ee (%) |
|---|---|---|---|---|
| 1 | (−)-sparteine | 5 | 80 | <3 |
| 2 | (S)-proline | 10 | <10 | 18 |
| 3 | (S)-monophos | 5 | <10 | 9 |
| 4 | (S,S)-chiraphos | 5 | <10 | −19 |
| 5 | N,N-Dibutyl-L-(+)-norephedrine | 7.5 | 88 | 21 |
| 6 | (+)-N-methylpseudoephedrine | 7.5 | 30 | 33 |
| 7 | quinidine | 7.5 | 64 | −42 |
| 8 | dihydroquinidine | 7.5 | 81 | −40 |
| 9 | (−)-N-methylephedrine | 7.5 | 68 | −22 |

Optimization reactions were carried out on 50 mg of quinol (XIII). The conversions shown In Table 6 were measured directly from HPLC data after 3 days. All ee measurements were measure by chiral HPLC using a (R,R)-Whelk Whelk O1 column, 1 mL/min, hexanes: IPA=92:8 at room temperature. The (−)-enantiomer of (+)-methyl 8'-acetylene ABA ester (XVIII) was obtained in excess in for entries 4, 7, 8, and 9.

The effects of additives on ECA were next investigated. Several additives were screened and the results are shown in Table 7. Among those screened, $Mg(OTf)_2$, NaOMe, LiOTf and AgOTf were all found to significantly enhance the enantiopurity of the product. The optimum loading of ligand: additive was found to be 5:2.

TABLE 7

Investigation of the effect of additives for the enantioselective synthesis of (+)-Methyl 8'-acetylene ABA (+)-(XVIII)

| Entries | (−)-Cinchonidine (eq) | EthynylMgCl (eq) | Additives | Conversions (%) | ee (%) |
|---|---|---|---|---|---|
| 1 | 2.5 | 7.5 | LiI (1 eq) | 93 | 56 |
| 2 | 2.5 | 7.5 | LiCl (1 eq) | 54 | 56 |
| 3 | 2.5 | 7.5 | $Al(OPr)_3$ (1 eq) | 56 | 54 |
| 4 | 2.5 | 7.5 | $Al(OEt)_3$ (1 eq) | 76 | 48 |
| 5 | 2.5 | 7.5 | $CdCl_2$ (1 eq) | 20 | 37 |
| 6 | 2.5 | 7.5 | $PBu_3$ (1 eq) | 20 | 53 |
| 7 | 2.5 | 7.5 | $PPh_3$ (1 eq) | 20 | 49 |
| 8 | 2.5 | 7.5 | PPTS (1 eq) | 47 | 51 |
| 9 | 2.5 | 7.5 | TFE (1 eq) | 79 | 55 |
| 10 | 2.5 | 7.5 | TFA (1 eq) | 22 | 58 |
| 11 | 2.5 | 7.5 | $Mg(OTf)_2$ (1 eq) | 85 | 64 |
| 12 | 2.5 | 7.5 | $MgSO_4$ (1 eq) | 75 | 58 |
| 13 | 2.5 | 7.5 | $Mg(OEt)_2$ (1 eq) | 72 | 51 |
| 14 | 2.5 | 6.5 | NaOH (1 eq) | 36 | 48 |
| 15 | 2.5 | 6.5 | TMSCN (1 eq) | 51 | 33 |
| 16 | 2.5 | 6.5 | NaHMDS (1 eq) | 90 | 53 |
| 17 | 2.5 | 6.5 | LDA (1 eq) | 84 | 56 |
| 18 | 2.5 | 6.5 | KOBut (1 eq) | 65 | 51 |
| 19 | 2.5 | 7.5 | NaOMe (1 eq) | 74 | 68 |
| 20 | 5 | 12.5 | NaOMe (2 eq) | 86 | 74 |
| 21 | 5 | 12.5 | $(C_2H_5)_4NPF_6$ (2 eq) | 82 | 48 |
| 22 | 5 | 12.5 | $MgF_2$ (2 eq) | 72 | 46 |
| 23 | 5 | 12.5 | $NaPF_6$ (2 eq) | 29 | 68 |
| 24 | 5 | 12.5 | $(C_4H_9)_4NPF_6$ (2 eq) | 72 | 58 |
| 25 | 5 | 12.5 | KOMe (2 eq) | 50 | 58 |
| 26 | 5 | 12.5 | LiOTf (2 eq) | 78 | 80 |
| 27 | 5 | 12.5 | NaOTf (2 eq) | 89 | 58 |
| 28 | 5 | 12.5 | KOTf (2 eq) | 68 | 51 |
| 29 | 5 | 12.5 | AgOTf (2 eq) | 65 | 76 |
| 30 | 5 | 12.5 | LiOMe (2 eq) | >95 | 53 |
| 31 | 5 | 12.5 | $NaSO_4$ (2 eq) | 90 | 55 |

Optimization reactions were carried out on 50 mg of quinol (XIII). The conversions shown in Table 7 were measured directly from HPLC data after 3 days. All ee measurements were measure by chiral HPLC using a (R,R)-Whelk O1 column, 1 mL/min, hexanes: IPA=92:8 at room temperature.

Additives possessing strong Lewis acid character were also tested but were detrimental to the starting quinol (XIII) at the reaction temperatures between −20 to −30° C. (TMSCl, $Mg(ClO_4)_2$, $Al(OTf)_3$, $Ba(OTf)_2$, $Ca(OTf)_2$, $ZnBr_2$, $ZnCl_2$, $NiC_{12}$, $Ni(acac)_2$, and $InC_{13}$) (Results not shown). Based on the turnover, LiOTf and NaOMe were selected as additives for further studies to optimize the ratio of ligand and ethynylMgCl as well as the temperature. The results of these optimization studies are shown in Table 8.

TABLE 8

Investigation of reaction parameters using LiOTF, H$_2$O and NaOMe as additives for the synthesis of (+)-Methyl 8'-acetylene ABA ester (+)-(XVIII)

| Entries | (−)-Cincho-nidine (eq) | Ethynyl MgCl (eq) | Additives | Temp. (° C.) | Conversion (%) | ee (%) |
|---|---|---|---|---|---|---|
| 1 | 5 | 12.5 | NaOMe (2 eq) | −30 | 86 | 80 |
| 2 | 5 | 12.5 | NaOMe (2 eq) | −20 | >95 | 76 |
| 3 | 5 | 12.5 | NaOMe (2 eq) | −30 | 45 | 9 |
| 4 | 5 | 10 | NaOMe (2 eq) | −30 | >95 | 79 |
| 5 | 5 | 15 | NaOMe (2 eq) | −30 | 84 | 78 |
| 6 | 5 | 20 | NaOMe (2 eq) | −30 | 87 | 77 |
| 7 | 2.5 | 7.5 | NaOMe (1 eq) | −30 | 67 | 73 |
| 8 | 2.5 | 7.5 | NaOMe (2 eq) | −30 | 37 | 27 |
| 9 | 1.25 | 6 | NaOMe (1 eq) | −30 | 44 | 23 |
| 10 | 5 | 12.5 | LiOTf (1 eq) | −30 | 81 | 67 |
| 11 | 5 | 12.5 | LiOTf (2 eq) | −30 | 80 | 79 |
| 12 | 5 | 12.5 | LiOTf (4 eq) | −30 | 65 | 76 |
| 13 | 5 | 12.5 | LiOTf (2 eq) | −20 | >95 | 78 |
| 14 | 5 | 12.5 | H$_2$O (1 eq) | −30 | 90 | 74 |
| 15 | 5 | 12.5 | H$_2$O (2 eq) | −30 | 30 | 33 |
| 16 | 5 | 12.5 | LiOTf (2 eq) + H$_2$O (1 eq) | −30 | 78 | 81 |
| 17 | 5 | 12.5 | LiOTf (2 eq) + H$_2$O (1 eq) | −30 | 87 | 80 |

Optimization reactions were carried out on 50 mg of quinol (XIII). The conversions shown in Table 8 were measured directly from HPLC data after 3 days. All ee measurements were measured by chiral HPLC using a (R,R)-Whelk O1 column, 1 mL/min, hexanes: IPA=92:8 at room temperature. For entry 3, ethynylMgBr was used instead of ethynylMgCl. (−)-Cinchonidine was recrystallized from hot ethanol in entry 17.

Referring to Table 8, conversion to (+)-(XVIII) was optimal at −20° C. and high enantioselectivity was obtained (see entries 2 and 13). It was found that good results could be obtained using NaOMe as the additive (entries 2 and 4), however, NaOMe gave less consistent results compared to LiOTf. Repeating conditions (entry 11) using LiOTf as the additive on a larger scale (4 g), the desired product was obtained in >95% conversion (4.2 g crude product (+)-(XVIII)) in 80% ee (see Table 7). Crystallization of the enantioenriched crude product as a yellowish brown oil using 1:1 acetone: water resulted in (+)-8'-acetylene ABA (+)-(IV) as white crystals with >98% chemical purity (by $^1$H NMR) and 93% ee.

We determined that addition of 1 mole equivalent of water to the chiral ligand prior to the ECA reaction resulted in high enantioselectivity. This was counter-intuitive for a Grignard reaction, however, using rigorously dried and purified (−)-cinchonidine resulted in low enantiopurity of the product. There are few authors who describe the effect of water in improving ee in an ECA reaction (A. Alexakis, C. Benhaim, S. Rosset, M. Humam, J. Am. Chem. Soc., 2002, 124, 5262; Delapierre, G.; Constantineux, T.; Brunel, J. M.; Buono, G. *Eur. J. Org. Chem.* 2000, 2507). We also determined that the order of addition of reagents, i.e. prior mixing of (−)-cinchonidine, LiOTf and water before addition of Grignard reagent, was required to achieve 80% ee. Hydrating the mixture of (−)-cinchonidine and LiOTf is likely required to generate the active chiral complex with ethynylmagnesium chloride. The structure of the putative chiral complex responsible for enantioselectivity in this system has not been investigated. One reference that describes the structure of the chiral species formed when mixing (−)-cinchonidine and Grignard reagents with transition metals was found (Cui, S.; Walker, S. D.; Woo, J. C. S.; Borths, C. J.; Mukherjee, H.; Chen, M. J.; Faul, M. M, *J. Am. Chem. Soc.* 2010, 132, 436), however, those involving no transition metals were not located. Under the preferred reaction conditions as described in entry 16 (Table 8), the ECA reaction was successfully performed in 16 g scale to give the desired product (+)-8'-acetylene ABA (+)-(IV) after LiOH hydrolysis in 74% yields over 2 steps in 80% ee.

EXAMPLE 1

Oxidation of Phenol Using Potassium Peroxymonosulfate

A well stirred suspension of potassium peroxymonosulfate (205 mmol) in acetonitrile (25 mL) and water (50 mL) was heated to 50° C. To this suspension was added the 2,6-dimethylphenol (41 mmol) and iodobenzene (4.1 mmol). After the reaction was complete, the mixture was allowed to cool to room temperature then filtered through a glass sintered funnel to remove the undissolved salts. The filtered salts were washed with hexanes/diethyl ether (9:1 v/v) until all of the yellow color had been washed off. The aqueous layers were extracted with hexanes/diethyl ether (9:1 v/v, 3×mL). The combined organic layers were dried with Na$_2$SO$_4$, filtered through a small plug of silica gel 60 and evaporated to dryness.

EXAMPLE 2

Production of 7,9-Dimethyl1,4-dioxaspiro[4.5]deca-6,9-dien-8-One or 2,6-Dimethyl-1,4-benzoquinone, mono ketal (VII)

2,6-Dimethylbenzoquinone (1.00 g, 7.4 mmol) was dissolved in (MeO)$_3$CH (1.69 mL, 15,4 mmol) and placed in a 40° C. bath. Ethylene glycol (35 mL) and TsOH.H$_2$O (141 mg, 0.74 mmol) were then added. When the internal temperature had reached 40° C., catalyst was added. The reaction was monitored by gas chromatography. After 2 h, the reaction was quenched using saturated NaHCO$_3$ (25 mL) to neutralize the acid. The product was extracted Into 10% ether/90% hexanes (v/v). The organic layers were dried with Na$_2$SO$_4$ and concentrated under reduced pressure. 2,6-Dimethyl-1,4-benzoquinone, mono ketal (VII) was isolated as a beige solid in 90% yield. Further purification was by recrystallization from hexanes.

EXAMPLE 3

Production of (2Z,4E)-5-(2',6'-Dimethyl-4',4'-ethylenedioxy-1'-hydroxycyclohexa-2',5'-dienyl)-3-methylpent-2,4-dien-1-ol (X)

Freshly distilled (Z)-3-methylpent-2-en-4-yn-1-ol (VIII) (11.7 g, 122 mmol) was dissolved in THF (500 mL) and cooled using a dry ice/ethanol bath under Argon for 30 min. with vigorous mechanical stirring. After the internal temperature reached −63° C., n-BuLi [2,5 M] (97.7 mL, 244 mmol) was slowly added using a syringe pump over 45 min. to give a pale yellow solution. After 4-5 h at −63 to −65° C., 2,6-dimethylbenzoquinone, mono ketal (VII) (20.0 g, 111 mmol), dissolved in THF (25 mL), was added slowly using a syringe pump to the reaction mixture over 1.5 h to give a yellowish green solution. The reaction mixture was stirred at this temperature for 4 h, then slowly warmed to −20° C. over 12 h. After all ketone (VII) had reacted (i.e. full conversion to intermediate as determinded by $^1$H NMR of an aliquot taken), Red-Al (33.8 mL, 111 mmol) was added to the reaction mixture slowly using a syringe pump at −20° C. over 15 min. The reaction mixture was then left stirring at that temperature for another 3 h (disappearance of starting material monitored by $^1$H NMR of an aliquot of the reaction mixture). The reaction was quenched with ice cold potassium sodium tartrate solution [0.75 M] (500 mL, 1:1 v/v) and was left stirring for another 1 h at 0 to 5° C. (internal temperature). This was followed by extraction with ether (3×500 mL) and drying of the combined organic layers over Na$_2$SO$_4$. The organic layer was concentrated to give crude alcohol (X) as yellow glue (32.6 g of crude (X), >95% purity by $^1$H NMR).

EXAMPLE 4

Production of Methyl-(2Z,4E)-5-(2',6'-dimethyl-1'-hydroxy-4'-oxocyclohexa-2',5'-dienyl)-3-methyl-pent-2,4-dienoate (XIII)

To a mixture of crude alcohol (X) (32.6 g, 117 mmol) in toluene (450 mL) [0.75 M] under Argon at ambient temperature was added manganese (IV) oxide (193 g, 2.22 mol) in one portion. The reaction was left mechanical stirring at room temperature for 12 to 24 h. After complete conversion of alcohol (X) to aldehyde (XI), monitored by thin layer chromatography and $^1$H NMR of an aliquot taken, methanol (224 mL, 5.55 mol), sodium cyanide (10.9 g, 222 mmol) and acetic acid (6.35 mL, 111 mmol) were added sequentially and the reaction mixture was left stirring for another 24 to 48 h. After the disappearance of aldehyde (XI) as seen by $^1$H NMR of an aliquot taken (i.e. full conversion to (XII)), the reaction mixture was filtered through a pad of Celite® (the residue was washed with ether [3×250 mL]). To the filtrate was added ice cold 1% HCl (200 mL) followed by stirring at 0 to 5° C. for 15 to 30 min. After deketalization was complete as determined by thin layer chromatography (i.e. full conversion to (XIII)), the crude product was extracted with ethyl acetate (3×500 mL). The combined organic layers were washed with saturated NaHCO$_3$, dried over magnesium sulfate and concentrated to give crude product (XIII) as a pale yellowish brown solid in 24.0 g, 83% yield (90-95% pure by $^1$H NMR) starting from ketone (VIII) (5 steps). Crude product (XIV) can be further purified by trituration with 50% ether in hexanes as required.

EXAMPLE 5

Production of Methyl-(2Z,4E)-5-(6'-ethynyl-1'-hydroxy-2',6'-dimethyl-4'-oxocyclohex-2'-enyl)-3-methylpenta-2,4-dienoate or Methyl-8'-acetylene ABA (±)-(XVIII)

To a cooled solution of ethynylmagnesium chloride (570 mL, 285 mmol) at −10° C. (internal temperature) under Argon, quinol (XIII) (15.0 g, 57.2 mmol) in THF (35 mL) was added over 1 h using a syringe pump. The reaction was left stirring for 24 hours (internal temperature, −10° C.). The reaction was quenched with slow addition of water (60 mL) causing the inorganic salts to form a precipitate. The resulting mixture was then filtered through a pad containing layers of Celite® and basic aluminium oxide. The residues were washed with ethyl acetate (2×250 mL) for maximum recovery. The filtrate was then dried, decolorized with activated carbon (5 g) and concentrated to produce crude product (±)-(XVIII) as a yellowish brown glue (15.1 g, 92% yield, ca. 90-95% purity by $^1$H NMR).

EXAMPLE 6

Production of (2Z,4E)-5-(6'-Ethynyl-1'-hydroxy-2',6'-dimethyl-4'-oxocyclohex-2'-enyl)-3-methylpenta-2,4-dienoic acid or 8'-acetylene ABA (±)-(IV)

To a solution of crude ester (±)-(XVIII) (13.4 g, 46.5 mmol) in THF (150 mL) was slowly added 150 mL of 1 M LiOH. The reaction mixture instantly turned black and was refluxed at 65° C. for 6 to 7 hours. After the hydrolysis was complete, as monitored by thin layer chromatography, the reaction mixture was ice cooled and extracted with ether (1×250 mL) to remove any organic impurities from the aqueous phase. The aqueous layer was then acidified with ice cold 37% HCl, extracted with dichloromethane (3×300 mL), decolorized with activated carbon (5 g), dried over magnesium sulfate and concentrated to give product 8'-acetylene ABA (±)-(IV) as a beige solid (10.0 g, 79%, >95% purity by $^1$H NMR).

EXAMPLE 7

Production of Methyl-(2Z,4E)-5-(6'-cyclopropyl-1'-hydroxy-2',6'-dimethyl-4'-oxocyclohex-2'-enyl)-3-methylpenta-2,4-dienoate or Methyl-8'-cyclopropyl ABA A few crystals of iodine were added to a suspension of magnesium powder (12.0 g, 500 mmol) in THF (800 mL). Cyclopropyl bromide (39.7 mL, 492 mmol) was added dropwise and the mixture was stirred for 12 hours at room temperature by which time most of the magnesium had been consumed. To the cooled solution of freshly prepared cyclopropylmagnesium bromide at −78° C. under Argon, quinol (XIII) (18.0 g, 68.7 mmol) in THF (35 mL) was added over 1 hour using a syringe pump, followed by addition of TMSCl (22.0 mL, 180 mmol). The reaction was left stirring for 5 hours at that temperature. After completion, the reaction was quenched with saturated ammonium chloride, extracted with ethyl acetate (3×250 mL), dried over magnesium sulfate and concentrated to provide desired crude methyl ester of 8'-cyclopropyl ABA as a yellow oil. The crude product was triturated with 50% ether in hexanes to give a highly pure but yellow precipitate of methyl-8'-cyclopropyl ABA (17.4 g, 82% yield).

EXAMPLE 8

Production of (2Z,4E)-5-(6'-cyclopropyl-1'-hydroxy-2',6'-dimethyl-4'-oxocyclohex-2'-enyl)-3-methyl-penta-2,4-dienoic acid or 8'-cyclopropyl ABA (V)

To a solution of methyl 8'-cyclopropyl ABA (6.0 g, 19.7 mmol) in THF (75 mL) was slowly added 75 mL of 1 M LiOH. The reaction mixture was refluxed at 75° C. for 5 hours. After the hydrolysis was complete, as monitored by thin layer chromatography, the reaction was ice cooled and extracted with dichloromethane (1×100 mL) to remove any organic impurities from the aqueous phase. The aqueous layer was then acidified with ice cold 37% HCl, extracted with dichloromethane (3×100 mL), dried over magnesium sulfate and concentrated to give product 8'-cyclopropyl ABA (V) as a beige solid (5.5 g, 96% yield, >95% purity by $^1$H NMR).

EXAMPLE 9

Production of (+)-Methyl-8'-acetelyneABA ester (+)-(XVIII)

(−)-Cinchonidine (91 g, 309 mmol, 5eq), LiOTf (19.3 g, 124 mmol, 2 eq) and $H_2O$ (1.2 mL, 66.6 mmol) were mixed together under argon at r.t. for 15 min. followed by addition of ethynylmagnesium chloride 0.5 M (1.54 L, 773 mmol, 11 eq). The reaction mixture was stirred at r.t. where the internal temperature of the reaction mixture was noted to be consistently between 32-34° C. After 4h, the reaction mixture was cooled in a −35° C. bath. When the internal temperature was noted to be −26° C., a THF solution of quinol (XIII) (16.2 g, 61,8 mmol, 1 eq) was added slowly to the reaction mixture over 2 h using a syringe pump. The reaction was left stirring for 4 days at −26° C. (internal temperature). After completion of reaction was confirmed by $^1H$ NMR and chiral HPLC of an aliquot taken [>95% conversion and 80% ee, retention time: $t_{major}$=27.4 min., $t_{minor}$ 36.2 min., R,R-Whelk column, 1 mL/min., hexane: isopropanol (92:8, v/v)], the reaction was quenched with 1.0 M aqueous citric acid (2 L), extracted with ethyl acetate (3×2 L), dried over magnesium sulfate and concentrated to afford the desired enantioenriched crude ester (+)-(XVIII) which was carried through to the next step without purification.

EXAMPLE 10

Production of (+)-8'-acetelyne ABA (+)-(IV)

Aqueous LiOH (200 mL, 1 M) was slowly added to a solution of 20 g of crude ester (+)-(XVIII) in THF (200 mL). The reaction mixture was refluxed at 75° C. for 5 h. After the hydrolysis was complete as confirmed by TLC, the reaction was ice cooled and extracted with ether (1×500 mL) to remove any organic impurities from the aqueous phase. The aqueous layer was then acidified with ice cold 37% HCl, extracted with dichloromethane (3×500 mL), dried over magnesium sulfate and concentrated to give the enantioenriched crude product (+)-(IV) as beige colored solid (12.76 g, 74% yield over 2 steps starting from (XIII), >95% purity as confirmed by $^1H$ NMR, 80% ee [retention time: $t_{major}$=11.5 min., $t_{minor}$ 15.9 min., (R,R)-Whelk O1 column, 1 mL/min. hexane (0.1% AcOH): isopropanol (88:12, v/v)], $[\alpha]_D^{25}$+237 (c 0.51, MeOH).

The invention claimed is:

1. A method of making a compound of formula 1

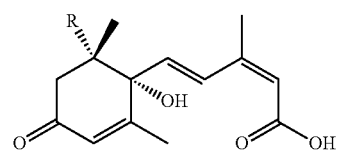

Formula 1 wherein R is alkyl, cycloalkyl, alkenyl or alkynyl, said method comprising:
   a) reacting 2,6-dimethylphenol (VI) with potassium peroxymonosulfate and a catalytic amount of iodobenzene to produce 2,6-dimethylbenzoquinone (XVI);
   b) reacting 2,6-dimethylbenzoquinone (XVI) with ethylene glycol and a catalytic amount of p-toluenesulfonic acid to produce 2,6-dimethylbenzoquinone, mono ketal (VII);
   c) reacting 2,6-dimethylbenzoquinone, mono ketal (VII) with (Z)-3-methylpent-2-en-4-yn-1-ol (VIII), followed by reduction of the propargylic triple bond to provide allylic alcohol (X);
   d) reacting allylic alcohol (X) with $MnO_2$ to form aldehyde (XI) followed by addition of an organic acid and an alcohol to produce ester (XII), followed by in situ deprotection of ester (XII) in the presence of an acid to produce quinol (XIII); and
   e) reacting quinol (XIII) with a carbanion magnesium halide, followed by ester hydrolysis to produce the compound of Formula 1.

2. The method of claim 1 wherein the reduction at step c is performed using Red Al.

3. The method of claim 1 wherein the organic acid is acetic acid and the alcohol is methanol.

4. The method of claim 1 wherein R is a methyl group and the carbanion magnesium halide is methylmagnesium chloride.

5. The method of claim 1 wherein R is a cyclopropyl group and the carbanion magnesium halide is cyclopropylmagnesium bromide.

6. The method of claim 1 wherein R is an alkynyl group and the carbanion magnesium halide is ethynylmagnesium chloride.

7. A method of making a (+)-enantiomer of a compound of formula 1

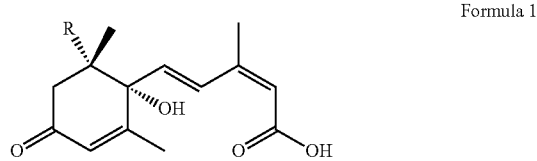

Formula 1 wherein R is ethynyl, said method comprising:
   a) reacting 2,6-dimethylphenol (VI) with potassium peroxymonosulfate and a catalytic amount of iodobenzene to produce 2,6-dimethylbenzoquinone (XVI);
   b) reacting 2,6-dimethylbenzoquinone (XVI) with ethylene glycol and a catalytic amount of p-toluenesulfonic acid to produce 2,6-dimethylbenzoquinone, mono ketal (VII);
   c) reacting 2,6-dimethylbenzoquinone, mono ketal (VII) with (Z)-3-methylpent-2-en-4-yn-1-ol (VIII), followed by reduction of the triple bond to provide allylic alcohol (X);
   d) reacting allylic alcohol (X) with $MnO_2$ to form aldehyde (XI) followed by addition of an organic acid and an alcohol to produce ester (XII), followed by in situ deprotection of ester (XII) in the presence of an acid to produce quinol (XIII); and
   e) reacting quinol (XIII) with (−)-cinchonidine, with an organic or inorganic salt, water and an ethynylmagnesium halide followed by ester hydrolysis to produce the (+)-enantiomer of the compound of Formula 1.

8. The method of claim 7 wherein the reduction at step c is performed using Red Al.

9. The method of claim 7 wherein the organic acid is acetic acid and the alcohol is methanol.

10. The method of claim 7 wherein and the ethynylmagnesium halide is ethynylmagnesium chloride.

11. The method of claim 7 wherein the organic or inorganic salt is lithium triflate.

12. The method of claim 1 wherein the carbanion magnesium halide is alkylmagnesium chloride, cycloalkylmagnesium chloride, alkenylmagnesium chloride or alkynylmagnesium chloride.

* * * * *